United States Patent [19]

Owen

[11] 4,185,491
[45] Jan. 29, 1980

[54] GAS MONITORS
[75] Inventor: Leslie J. Owen, Porthcawl, Wales
[73] Assignee: British Steel Corporation, England
[21] Appl. No.: 859,522
[22] Filed: Dec. 12, 1977
[30] Foreign Application Priority Data
Jan. 10, 1977 [GB] United Kingdom .................... 779/77
[51] Int. Cl.² ............................................ G01N 27/14
[52] U.S. Cl. .................................... 73/27 R; 340/634
[58] Field of Search ............. 73/23, 27 R; 340/237 R, 340/634

[56] References Cited
U.S. PATENT DOCUMENTS

| 3,695,848 | 10/1972 | Taguchi | 73/27 R |
| 3,877,291 | 4/1975 | Hoppesch et al. | 73/27 R |
| 3,895,367 | 7/1975 | Visser | 340/237 R |
| 3,906,473 | 9/1975 | Le Vine | 370/237 R |
| 3,932,807 | 1/1976 | Wilson | 73/23 |
| 3,950,739 | 4/1976 | Campman | 340/237 R |
| 4,000,650 | 1/1977 | Snyder | 73/290 V |

FOREIGN PATENT DOCUMENTS 1374575 11/1974 United Kingdom .................... 73/27 R Primary Examiner—Daniel M. Yasich
Attorney, Agent, or Firm—Bacon & Thomas

[57] ABSTRACT

A gas sensor incorporating a sensor element of the heated semi-conductor type has a heater for the element connectible to a variable power source, the output of which is responsive to the concentration of gas under test.

10 Claims, 1 Drawing Figure

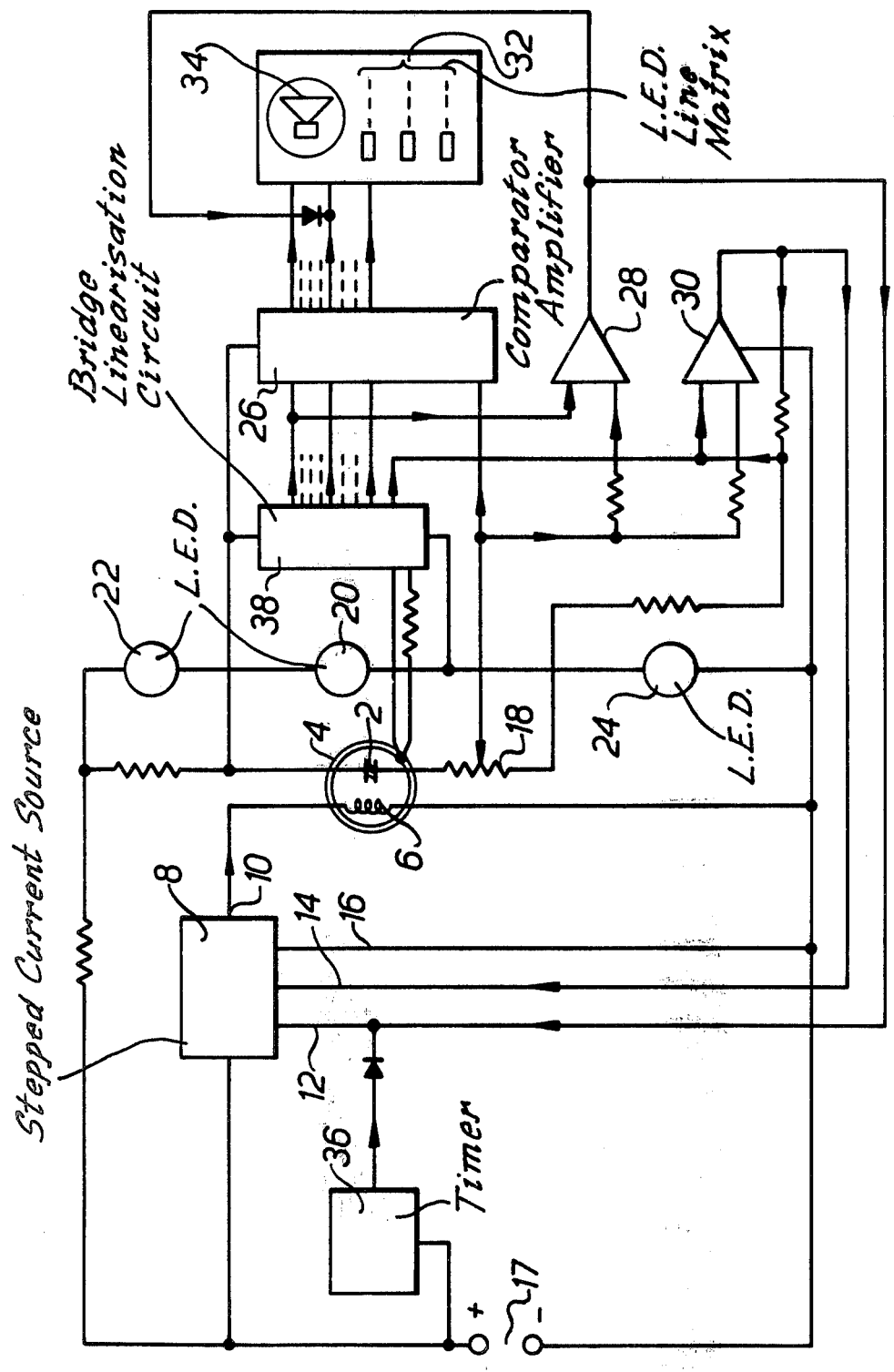

GAS MONITORS

This invention relates to gas monitors, and is particularly, although not exclusively, concerned with monitors capable of detecting the existence in an air ambient of toxic gases such as carbon monoxide.

The present invention is concerned with monitors in which the gas sensor comprises an electrically heated semi-conductor element whose resistance varies as a function of adsorbed gas. Typically such elements contain a suitable doped metal oxide and examples of this type of sensor are disclosed in UK Patent Specification No. 1374575 and in "Solid State Detectors for Carbon Monoxide"—Ann. occup. Hyg. Vol. 18 pp 63–68.

The FIGURE is a schematic diagram of a gas monitor of the present invention.

Sensors of the type with which the present invention is concerned generally are incorporated into one arm of a bridge or other resistance-sensitive network so that changes in resistance brought about by variation in the concentration of a constituent in the ambient surrounding the sensor can be detected and registered. The relative sensitivity of the sensor to different constituents can be modified by selecting the operating temperature of the semiconductor element and a temperature for detecting specific gases is achieved by adjusting the level of the sensor heating current.

It has been found, however, that the sensor temperature necessary to maintain the sensor free of absorbed gas provides relatively low sensitivity for most gases. Such lack of sensitivity is particularly apparent in the case where the concentration of carbon monoxide in the air ambient of an industrial environment is to be monitored, and it is one object of the present invention to improve the sensitivity of a gas monitor.

According to its broadest aspect, the present invention provides a gas monitoring device incorporating a sensor of the Taguchi heated semi-conductor type having a heater for the element sensor connectible to a stepped variable output power source, the output of which is responsive to the concentration of the gas under test.

It has been found for most gases that by lowering the temperature of the sensor an increase in sensitivity can be obtained notwithstanding the progressive sensor poisoning which occurs by the more rapid absorption of gas at the lower temperature. The period over which the sensor can be operated at the lower temperature depends both upon the temperature drop which is produced as well as upon the concentration of the selected gas which is being monitored.

In order to avoid unnecessary operation of the sensor at the reduced temperature, the stepped power source conveniently is adapted to reduce the normal quiescent power input to the heater only when the concentration of the selected gas rises above a selected level.

After operation at the reduced temperature, the increased quantity of gas absorbed in the sensor may be expelled by increasing the sensor temperature above the normal quiescent operating level at which equilibrium is maintained between absorbed and expelled gas.

In a preferred embodiment of the invention the stepped variable output power source for the sensor heater also is arranged to respond to a further control signal representative of a concentration of the selected gas above a second higher threshold at which the sensor absorbs gas at a rate producing more rapid poisoning. In this case the stepped power source automatically increases the power applied to the heater above the quiescent level, to raise the sensor to a temperature at which the rate of gas absorption is reduced. While this higher temperature does in general produce a reduction in sensitivity, this reduction is compensated for by the higher concentration of the gas being monitored.

An embodiment of the invention will now be particularly described by way of example with reference to the accompanying drawing which is a schematic circuit diagram of a carbon monoxide monitor incorporating multi-voltage heating of the sensor element.

Referring to the drawing, the monitor includes a sensor 2 of the Taguchi semi-conductor type contained in a housing 4, which has a built-in resistance heater 6. The heater 6 which is effective to maintain the sensor 2 at the selected temperature is energised from a stepped, variable output current source 8. Source 8 is capable of providing a stepped power output at 10 in response to selective activation of control inputs 12, 14, and 16.

A primary or secondary battery 17 energises the current source 8 together with the remainder of the circuit shown in the FIGURE.

Sensor 2 is incorporated into one arm of a bridge circuit including potential divider 18 in known fashion. Bridge circuits incorporating sensors are known, a typical example being U.S. Pat. No. 3,932,807. The voltage output from the tap of divider 18 will reflect the resistance of the sensor 2 which is in turn representative of the concentration of carbon monoxide at the active surface of the sensor.

Current input to the bridge circuit is conventional and is by way of a stabilised potential difference derived from a light emitting diode (LED) 20 which displays zener diode characteristics. Diode 20 forms part of a series chain of LED's 20, 22, 24 connected between the positive and negative rails of the battery supply 17. Diode 22 provides an indication of the charge level of battery 17 where diode 24 provides a potential drop enabling diodes 20 and 22 to provide the operating potential differences required.

The output from potential divider 18 is applied simultaneously to known differential comparator amplifier 26 and to differential amplifiers 28 and 30. Differential amplifiers 28 and 30 are arranged to provide voltage outputs when the input from divider 18 respectively exceeds relatively lower and higher levels. Amplifier 28, for example, is arranged to provide an output when the input signal exceeds a value representative of a first lower threshold level of carbon monoxide of about 25 p.p.m. in the ambient being monitored. With the first lower threshold exceeded, the output from the amplifier 28 constitutes a control signal via line 12 effective to switch the stepped current source 8 from a quiescent output voltage of 5.0 volts to a lower output voltage of 4.25 volts. With the sensor of the Taguchi type (Type 812 manufactured by Figaro Japan, for example), a heater voltage of 5.0 volts produces a sensor temperature at which adsorbed and expelled carbon monoxide are maintained substantially in equilibrium but with a relatively low sensitivity to carbon monoxide. At the temperature produced by the reduced voltage of 4.25 volts, the sensitivity to carbon monoxide is increased by a factor of about 5 notwithstanding that progressive poisoning of the sensor occurs due to a higher rate of gas adsorption accompanied by a lower rate of emission. Unless the carbon monoxide concentration exceeds about 800 p.p.m. the lower temperature can be maintained for a sufficient period to provide meaningful measurement without significant loss of sensitivity.

Variations in the concentration of carbon monoxide, reflected in the output voltage from potential divider 18, are applied to comparator amplifier module 26. Amplifier module 26 has a plurality of individual amplifier circuits effective sequentially to activate a line matrix 32 of light emitting diodes which provide an indication of concentration. Selected outputs of amplifier 26 and representative of specific concentrations, are effective to activate one or more alarm devices such as an audio transponder 34. The audio transponder may be replaced by a light emitting device which operates continuously or intermittently.

An output from potential divider 18 representative of a high concentration of carbon monoxide, for example 800 p.p.m. or more, sufficient to produce rapid poisoning of the sensor 2, is effective to activate differential amplifier 30 which, in turn, activates the stepped current source 8 via line 14, to produce a higher output voltage of 6.5 volts to the heater. As hereinbefore described, the increased sensor temperature at this input to the heater, while providing a lower sensitivity to carbon monoxide, significantly reduces the rate at which the sensor becomes poisoned, and maintains stability during the period in which measurement is being made.

To maintain the appropriate high level display, notwithstanding the reduction in the sensitivity of the sensor at the high temperature operation produced by a heater voltage of 6.5 volts, a signal is applied directly from the higher level control signal to the display circuit to maintain it in alarm condition.

A timer 36, activated when the circuit is first switched on, is effective to control the current source 8 to provide a heater voltage which maintains the sensor 2 at a temperature at which it can expel gas adsorbed during the preceding non-operating period.

A bridge linearisation circuit 38 is connected to a comparator amplifier 26 and to differential amplifiers 28 and 30 in known fashion to ensure a constant sensitivity of the monitor as a whole, notwithstanding changes of sensitivity in the sensor 2 brought about by changes in operating temperature. Further compensation for change of sensitivity with temperature may be provided by a thermistor responsive to the temperature of the sensor housing and effective to apply a compensating signal to the circuit 38, in known fashion.

To ensure that the heater voltage returns to 5.0 volt operation when the gas concentration falls to the level at which the first change of heater voltage occurs, it is necessary to arrange that reverse switching occurs at a level which is increased in direct relationship to the increase in sensitivity produced by the initial reduction in heater voltage. This may be achieved by feeding a signal from the 4.25 heater control signal to the first switching reference level of the comparator amplifier.

It will be appreciated that while the invention has been described with reference to the detection of carbon monoxide in air, it is equally applicable to the detection of other gases. It will also be appreciated that the temperature at which the sensor is operated may be varied according to the gas being detected and according to the specific sensitivity which is required in different ambients.

We claim:

1. In a gas monitoring device having a gas sensor of the semi-conductor type, a heating device located adjacent to said gas sensor such that increasing or decreasing the temperature of the heating device increases or decreases the temperature of the gas sensor, and a power source for energizing the sensor and the heating device, the improvements comprising:
  (a) first comparing means to compare an output from said sensor to a first gas concentration threshold value and provide a first output signal when said sensor output exceeds said first threshold value;
  (b) second comparing means to compare the sensor output to a second gas concentration threshold value and provide a second output signal when said sensor output exceeds said second threshold value; and,
  (c) stepped current source means connected to said power source, said heating device, and said first and second comparing means so as to maintain said heating device and, consequently, said sensor at a quiescent temperature under normal operating conditions and wherein said stepped current source reduces the power supplied to the heating device to thereby lower its temperature and the temperature of said sensor upon receipt of a signal from said first comparing means and increases the power supplied to the heating device to thereby raise its temperature and the temperature of the sensor upon receipt of a signal from said second comparing means.

2. The improved gas monitoring device of claim 1 wherein the second gas concentration threshold value is of greater magnitude than said first gas concentration threshold value.

3. The improved gas monitoring device of claim 2 wherein said first comparing means comprises a differential amplifier.

4. The improved gas monitoring device of claim 3 wherein said second comparing means comprises a differential amplifier.

5. The improved gas monitoring device of claim 1 wherein the stepped current source means supplies three discrete levels of power to said heating device: a first, intermediate quiescent level, a second, lower power level upon receipt of a signal from said first comparing means and a third, higher power level upon receipt of a signal from said second comparing means wherein said third power level is greater than said first intermediate quiescent level.

6. The improved gas monitoring device of claim 5 wherein the output of said stepped current source operating at the intermediate quiescent level is approximately 5 volts; the output while operating at second lower power level is approximately 4.25 volts; and the output while operating at the third higher level is approximately 6.5 volts.

7. The improved gas monitoring device of claim 1 further comprising alarm means connected to said sensor, said alarm means being activated when the gas concentration exceeds a predetermined level.

8. The improved gas monitoring device of claim 1 further comprising timer means connected to said power source and said stepped current source such that said stepped current source is initially operated at its highest power output level for a predetermined period of time to raise the temperature of the heating device and the sensor so as to decontaminate the sensor by driving off the gases absorbed during a period of inoperativeness.

9. The improved gas monitoring device of claim 1 wherein the first gas concentration threshold value is approximately 25 p.p.m.

10. The improved gas monitoring device of claim 9 wherein the second gas concentration threshold value is approximately 800 p.p.m.

* * * * *